(12) United States Patent
DeFriez et al.

(10) Patent No.: US 7,337,683 B2
(45) Date of Patent: Mar. 4, 2008

(54) INSITU INERTIAL PARTICULATE SEPARATION SYSTEM

(75) Inventors: Herbert H. DeFriez, Carpenteria, CA (US); Clifford Gordon, Carpenteria, CA (US); David Whitcomb, Santa Barbara, CA (US); Joseph Gregoria, McHenry, IL (US)

(73) Assignee: M & C Products Analysis Technology, Inc., Ventura, CA (US)

( * ) Notice: Subject to any disclaimer, the term of this patent is extended or adjusted under 35 U.S.C. 154(b) by 237 days.

(21) Appl. No.: 11/116,996

(22) Filed: Apr. 27, 2005

(65) Prior Publication Data

US 2005/0241416 A1 Nov. 3, 2005

Related U.S. Application Data

(60) Provisional application No. 60/566,320, filed on Apr. 28, 2004.

(51) Int. Cl.
*G01N 1/00* (2006.01)

(52) U.S. Cl. .................. 73/863.23; 73/863.25

(58) Field of Classification Search .......... 73/1.06, 73/1.07, 863.21, 863.23, 863.24, 863.25, 73/863.11, 863.12
See application file for complete search history.

(56) References Cited

U.S. PATENT DOCUMENTS

| | | | |
|---|---|---|---|
| 3,367,850 A * | 2/1968 | Johnson .................. 205/788 |
| 3,559,491 A | 2/1971 | Thoen et al. | |
| 3,593,023 A * | 7/1971 | Dodson et al. ............. 250/430 |
| 4,161,883 A | 7/1979 | Laird et al. | |
| 4,379,412 A | 4/1983 | Wood | |
| 4,481,833 A | 11/1984 | Bajek | |
| 4,484,481 A | 11/1984 | Laird et al. | |
| 4,578,986 A | 4/1986 | Navarre | |
| 4,856,352 A | 8/1989 | Daum et al. | |
| 4,912,985 A | 4/1990 | Daum et al. | |
| 4,974,455 A | 12/1990 | McGowan et al. | |
| 5,039,322 A * | 8/1991 | Holzl ........................ 55/302 |
| 5,178,022 A | 1/1993 | Tomlin | |
| 5,237,881 A | 8/1993 | Ross | |
| 5,297,432 A | 3/1994 | Traina et al. | |
| 5,302,191 A | 4/1994 | Koutrakis et al. | |
| 5,456,104 A * | 10/1995 | Rosen ...................... 73/29.02 |
| 5,777,241 A * | 7/1998 | Evenson .................. 73/863.11 |
| 6,324,895 B1 | 12/2001 | Chitnis et al. | |
| 6,736,883 B2 | 5/2004 | Sjostrom et al. | |
| 2001/0032519 A1* | 10/2001 | Liu et al. ................. 73/863.23 |

* cited by examiner

*Primary Examiner*—Robert Raevis
(74) *Attorney, Agent, or Firm*—Koppel, Patrick, Heybl & Dawson; Michael J. Ram

(57) ABSTRACT

A sampling system for separating gaseous samples from a gas stream containing particulate matter and transporting the gaseous samples to a location outside of the flowing gas stream comprises an inertial filter mounted on the end of a hollow probe, the inertial filter positioned within the flowing gaseous stream. The inertial filter comprises a filter media mounted within a tube such that a portion of the particulate-containing gaseous steam flows through an annular space between the filter media and the tube wall, the gas to be sampled passes through the filter media into an inner space and the filtered gas is then delivered through the hollow probe to analytical devices external to the space containing the flowing gas stream, such as a flue stack.

16 Claims, 3 Drawing Sheets

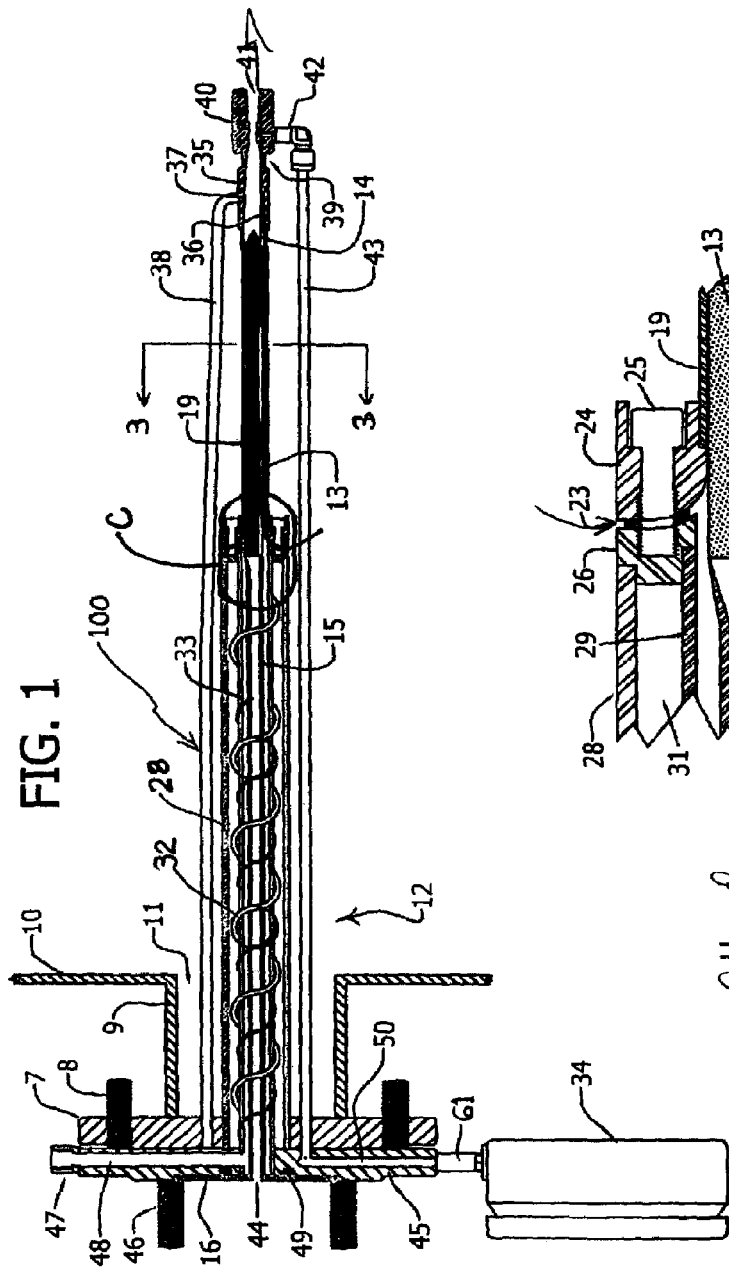
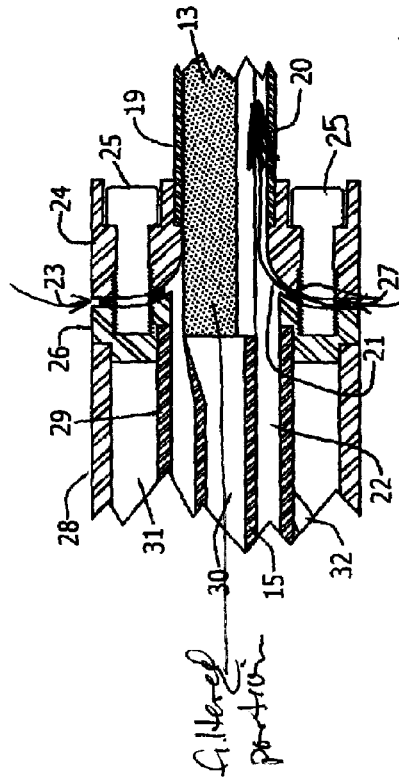

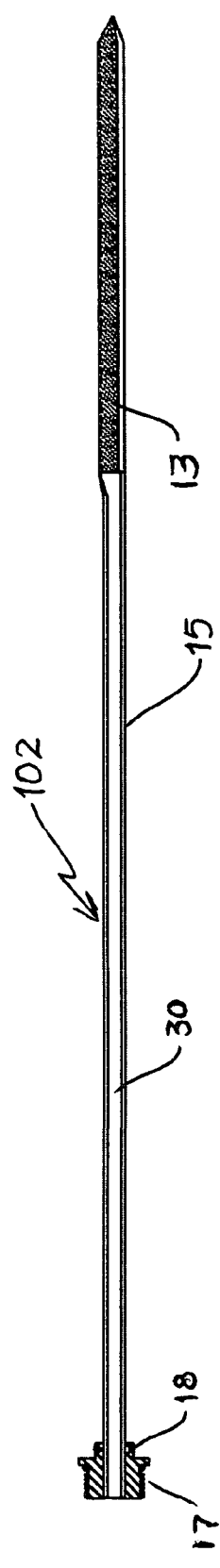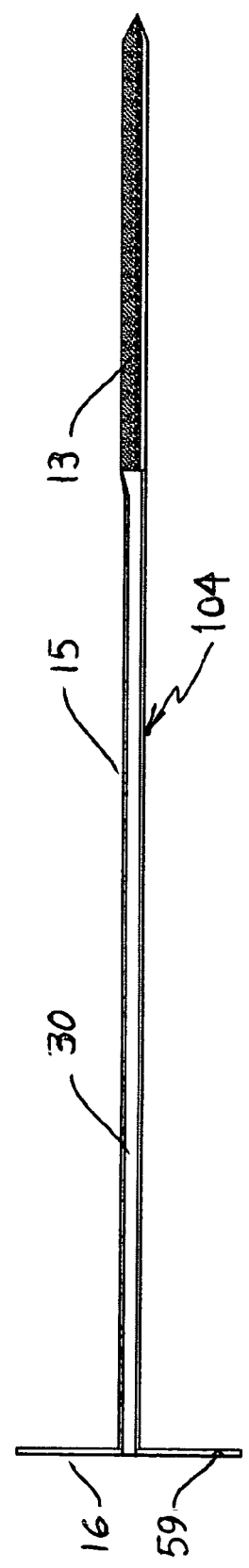

INSITU INERTIAL PARTICULATE SEPARATION SYSTEM

Benefit is claimed of Provisional Patent Application Ser. No. 60/566,320 filed Apr. 28, 2004.

FIELD OF INVENTION

This invention generally relates to an extractive gas sampling system which employs a non-clogging, flow-through inertial filter for use in analysis of process gas in process vessels, process gas ducts and fossil fuel and/or alternative fuel combustive gas streams being vented through a stack. In particular, a new system is described for sampling a gas containing a particulate solid phase which may be reactive, such that all or substantially all of the solids are removed while leaving the gas phase composition essentially unchanged. Thus, a representative particulate free gas sample is obtained so that its composition can be determined by standard gas analysis technique.

DESCRIPTION OF THE PRIOR ART

An important category of extractive gas sampling relates to the compliance monitoring requirements enforced by the United States Environmental Protection Agency (EPA). Operators of many sources of air pollution, such as fossil-fueled power plants, incinerators, metal smelters, and cement kilns, are required to monitor levels of certain gaseous species that are released into the atmosphere. These species include sulfur dioxide, nitrogen oxides, carbon monoxide, carbon dioxide, oxygen, mercury, lead, sulfur and certain other emissions deemed important to Public Health. The current EPA standards for compliance monitoring systems are delineated in Volume 40 of the Code of Federal Regulations.

The gas streams to be monitored typically have certain intrinsic characteristics which complicate testing. For example, combustion sources can contain between 6% to 20% by volume of water of combustion that results in a sample dew point well above that of normal ambient temperatures. Also, after-scrubber gas streams often contain significant amounts of condensed moisture in the form of entrained water droplets and fog. Acid gases, such as sulfur dioxide and sulfur trioxide are also generally present. Additionally, the combustion gas streams invariably contain large quantities of particulate debris such as soot and fly ash from fossil fuels. Process streams can also contain entrained catalytic materials or materials being produced in the process vessel such as cement in cement kilns.

Due to the sensitivity of the instrumentation incorporated in the modern multi-component gas analyzers, it is necessary to remove substantial portions if not all of the particulate matter entrained in the process gas sample without adversely affecting the gaseous components that are to be analyzed. Typically, elimination of particulate matter is accomplished by separating the gases from the solid matter in the gas stream using a conventional filter. In this extractive method, a probe is projected a suitable distance through the stack wall or vessel wall into the stack stream or vessel head space. The inlet to the probe through which the sample is withdrawn is fitted with a porous filter. Past practice has been to use a filter capable of screening out particles of greater than 5-30 micron size. Such filters clog rapidly in the severe environment to which they are exposed necessitating frequent replacement or cleaning. Stack probes are often mounted high above the ground, making filter replacement hazardous and time consuming. Some relief in replacement and cleaning effort is gained by providing automatic periodic blowback through the filter to dislodge entrapped particles. However, blowback does not provide effective long term purging in filters having a porosity below about 100 micron. Therefore, periodic replacement of the filter is still required. The most significant problem with this approach is that the sample gas must flow through any accumulated filter cake on the filter. It has been demonstrated that certain reactions between the filter cake and the sample gas can occur, resulting in removal of a constituent of analytical interest. When this occurs, the collected gases will not be representative of the bulk, stack, or vessel gases.

One of the methods of reducing the amount of filter cake that the sample gas must flow through is to use an inertial filter, as described by Laird (U.S. Pat. No. 4,161,883), Wood (U.S. Pat. No. 4,379,412), Laird (U.S. Pat. No. 4,484,481) and Ross (U.S. Pat. No. 5,237,881). With the traditional inertial filter approach, particles are entrained in a high velocity axial gas stream flowing past a tangential filter; particulates are precluded from deposition on the porous filter walls or from penetrating there through by the ballistic effect of particle inertia, hence the name "inertial" filter. The low radial velocity of such devices also inhibits particles from penetrating the porous wall. An example of such devices is manufactured by Mott Metallurgical Corporation, Farmington Industrial Park, Farmington, Conn. and are disclosed in their brochure entitled Inertial Gas Sampling Filter Systems DB 4600.

In U.S. Pat. No. 4,161,883, "Conditioning Assembly for Continuous Stack Monitoring", to J. C. Laird et al. there is disclosed a probe assembly for the extraction of gas samples from a gas stream that is heavily laden with particulate matter. The Laird et al. probe includes an inertial filter comprising a sintered metal porous sleeve through which a high velocity gas stream is induced to flow by an ejector. The porous sleeve is surrounded by a larger diameter cylinder from which gas samples are extracted for analysis. According to Laid et al, the extracted gas samples are substantially free from particulates because solids entrained in the high velocity stream flowing axially through the filter sleeve possess a high momentum and the sample gas is extracted orthogonally to the axial stream at a relatively low rate so as not to significantly change the momentum of the particles. It has been found, however, that in certain installations involving gases with very high concentrations of particulates the Laird et al. type probe is subject to filter cake accumulations forming on the course prefilter, subjecting the gases entering the inertial part of the filter to reaction and/or absorption on this prefilter cake. In addition, no provision is made for cleaning the inertial filter sleeve by blowback. It is therefore necessary from time to time to disassemble the probe for cleaning of the filter sleeve.

In U.S Pat. No. 4,379,412, "Sampling Probe for Stack Gas Monitoring System", to R. D. Wood and U.S. Pat. No. 4,484,481, "Gas Sampling Extractor and Conditioning Assembly", D. G. Laird et al, the problems with prefilter cake accumulation and inertial filter blowback are addressed but additional operational problems are introduced by the overall design. Both probes are rather complex mechanical designs that might be difficult to service at stack level installations. In addition, the designs require the removal of the high velocity gas that passes the inertial filter to the outside the stack. This can be problematic if the educted gas is reactive, flammable or toxic. Both patents show the flow path for the gas making a sharp 90 or 180-degree turn, ostensibly for reintroduction into the stack. This pneumatic disturbance is known to deposit particulates on the outside radius of the tube, eventually clogging the return path and stopping the inertial filtration process altogether.

In U.S. Pat. No. 5,237,881, "Inertial Dilution Filter Probe", to T. C. Ross, an additional complication is added by moving the inertial filter outside the stack or duct. By moving the inertial portion of the filter to a location outside the stack or duct, whatever temperature or pressure related effects that were occurring in the duct must be duplicated outside the stack or duct to prevent moisture condensation and/or changes in continuing reaction kinetics in order not to modify the collected sample and make the sampled material inconsistent with the bulk gases in the stack or duct.

U.S. Pat. No. 6,736,883 to Sjostrom et al. is directed to a system for measuring mercury in a flue gas stream containing particulates. The system utilizes an inertial filter system incorporating a sintered tube mounted external of the stack and temperature sensors and controllers to maintain the temperature of the sintered tube at substantially the same temperature as the gas stream in the stack.

SUMMARY

The present invention provides a sampling probe assembly for an industrial gas monitoring system which is capable of withstanding continuous exposure to high concentrations of particulate matter in such a manner that little, if any, filter cake build up occurs on the filter element through which sample gas must pass.

The gas sampling probe assembly is intended to supply substantially particulate-free gas samples for analysis.

In a preferred embodiment, the probe provides a pneumatic flow path through the inertial filter assembly that minimizes or eliminates particulate buildup on critical surfaces where the particulate material cannot be removed by an external blowback mechanism (included in the flow path design).

Additionally, the entire inertial filter is intended to be easily removed from the sampling assembly, preferably without tools, facilitating maintenance operations when necessary.

One embodiment provides a path for external calibration gas to flow in such a way as to displace the stack or duct gas and allow the system to draw this known gas through the inertial filter element and whatever filter cake is present, thus providing information on system bias.

The system provides a sampling probe assembly where all filtration and return of educted gas occurs inside the stack or duct at duct temperature and pressures so as to not introduce external variables into the duct kinetics.

As an option, the motive fluid for the eductor pump may be filtered process gas (or liquid) so that foreign materials are not introduced into the stack or process duct.

A further improvement provides a pressure port downstream of the inertial filter element to allow monitoring of the eductor vacuum and/or filter cake buildup.

The clean sample gas collected from inside the inertial filter alternatively can be heated as it is transported toward a collection point outside the stack or duct so as to keep reactive materials or water from condensing in the sample line.

Various cross sectional shapes for the inertial filter element are provided so that it can be adjusted to obtain the maximum amount of inertial filtration with the minimum amount of motive air to the eductor pump while still maintaining a fully turbulent flow in the sampling annulus.

A further aspect of the sampling probe assembly design is that it can be mounted to provide access to process streams and interface with the sample extraction system through standard pattern flanges, thus providing ease of integration with existing extractive probe designs.

BRIEF DESCRIPTION OF THE DRAWINGS

FIG. 1 is a cross-sectional view of an embodiment of a filtered extractive gas sampling system incorporating features of the invention mounted in a stack wall.

FIG. 2 is an enlarged view of the circled portion of FIG. 1 showing the pneumatic entrance to the inertial filter flow tube.

FIG. 7 is a cross-sectional view of a first embodiment of a removable filter assembly for a probe body.

FIG. 8 is a cross-sectional view of a second embodiment of a removable filter assembly using a standard flange seal.

DESCRIPTION OF PRESENT PREFERRED EMBODIMENTS

Figure 6:
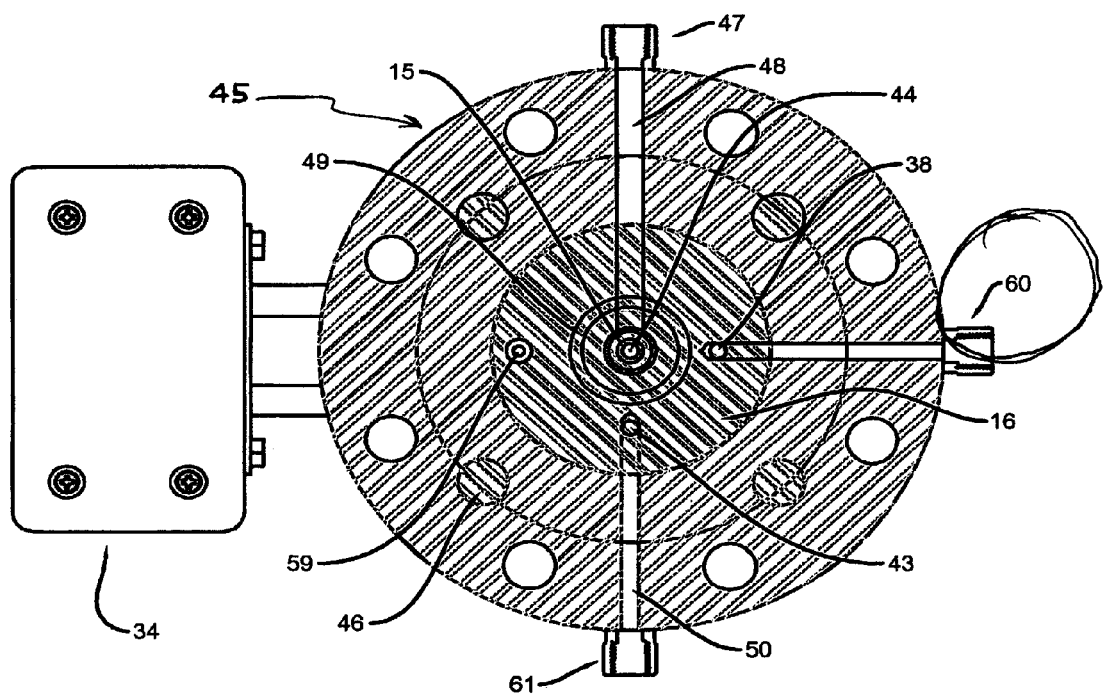
FIG. 6 is a side view of a standard pattern flange showing the location of input and output lines associated with the filter system.

FIGS. 1, 2 and 6 illustrate an embodiment of the gas sampling and extraction system incorporating features of the invention. A stack wall 10 is shown with a breach 11 therein which terminates at a standard flange 7. The probe 100 comprises a support flange 45 external to the stack, a body tube 28 attached to the support flange 45, downstream and upstream collets 24, 26 at the internal end of the body tube 28, the collets, 24, 26 forming the sampling slit 23 and inertial filter flow tube 19 on the internal end of the body tube. Attached to the end of the flow tube 19 is a transition piece 35, forming the pneumatic transition and vacuum port, and eductor pump 40 all of which extends into the interior of the stack, resting in the flowing duct gases 12. Gas 12 moving within the stack is drawn by the sample eductor pump 40 into the sampling slit 23. An example of a suitable eductor pump 40 is the (AIRVAC Technical Service). The gas then follows a pneumatically smooth path 21 (best shown in FIG. 2) into the inertial filter annulus 20 that is formed between the inertial filter flow tube 19 and the chosen filter element 13. Sample gas is extracted through the filter element 13 centered in the inertial filter flow tube 19 through an internal tubular space 30 that exists both in the filter element 13 and in the inertial filter extension tube 15. Sample gas then exits to external processing and analytical apparatus at flange port 44.

Figures 3, 4, 5:
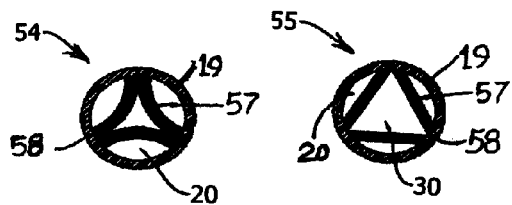
FIGS. 3, 4 and 5 are transverse sectional views of three alternative filter designs inside the flow tube, taken along line 3-3 of FIG. 1.

As shown in the FIGS. 3, 4 and 5, the inertial filter 13 is preferably manufactured by joining three sections of flat or arced sintered metal sheet 57 together at their edges 58 (the apex of the triangle) to form various hollow filters that have a smaller internal volume and external volume (i.e., an annular space) than the internal diameter of tube 19. The filter element 13 is thus centered within tube 19 to form different internal shaped three-sided filter assemblies 54, 55, 56 in which the three apex of each may contact the tube inner wall. The annulus 20 between this filter element 13 and the filter flow tube 19 provides the flow path for the stack or duct gas that is drawn down the annulus 20 by the vacuum created by the eductor pump 40. The motive fluid to operate the eductor pump is supplied through the fitting 42 and the supply line 43, coming in through the flange connection 61 and down the bore hole 50 from an external regulated supply (not shown). The extension line 15 attached to the inertial filter element 13 brings the sampled gas to the exterior of the stack via flange port 44. The filter media making up the filter element 13 preferably has a nominal porosity of between 0.2 and 2 microns. Depending on the cross sectional area of the shape chosen for the filter media, the eductor pump 40 is operated by a gas stream supplied at a pressure of 15-30 psig to provide a flow velocity of at least 80 ft./sec. through the annulus 20. Annulus 20 may suitably have an internal area of 0.05 to 0.1 sq.in. resulting in a volume flow of approximately 1.8 to 3.4 cu. ft./min. or 50-96 L./min. at a flow velocity of 80 ft./sec. A moderate vacuum is applied to flange port 44 by a sampling pump (not shown) located at a remote monitoring station extracting sample gas from the internal tubular space 30. The flow of sample gas in the extension tube 15 is at a low rate of from about 0.1 L./min. to not more than about 5 L./min. Such a low sample gas flow has a negligible effect on the momentum of particles entrained in the stream flowing through annulus 20. As a result, the gas sample is substantially free of all particulate matter.

While a three-sided filter configuration is preferred, one skilled in the art, based on the teachings herein, will recognize that other shapes and assemblies with more than three sides can be issued to accomplish similar flow, volume and area relationships. By adjusting the cross sectional shape of the filter media of the inertial filter element 13, as indicated by FIGS. 3, 4 and 5, one can adjust the Reynolds's number of the moving stream to remain in fully turbulent flow with any chosen eductor pump 40 flow rate, resulting in little tendency for particles to enter and become entrapped in the pores of the media filter element 13. Any particles adhering momentarily to the exterior surface of the media of filter element 13 are scoured away by the turbulent, high velocity particles of the passing stream. The system components, and in particular the filter element 13, extension tube 15, flow tube 19, collets 24, 26, body tube 28, internal tube 29, and transition piece 35 as well as the eductor pump 40 may be constructed of any inert material suitable for the temperature and operating environment. Examples of suitable materials for this purpose are glass, ceramics, corrosion resistant metal alloys such as Hastalloy C-22 or 276 and corrosion resistant polymeric materials such as Teflon or Kynar.

Operation of the system is aided by the smooth flow paths taken by samples of the duct gas 12 passing the inertial filter element 13 such that buildup of particles does not occur. Sample gas enters the system through a sampling slit 23 which is formed by an upstream flow collet 26 held in close proximity to the downstream flow collet 24 by bolts 25 and standoffs 27. No coarse filter is necessary in this flow path. The duct gas bends along the smooth path 21 into the inertial filter annulus 20 where the actual inertial filtration occurs. As the gas passes the end of the filter element 13, a tailpiece 14 recombines the three streams (created from the shape of the media of filter element 13) back into one stream with minimum turbulence. The gas then enters a transitional piece 35, which is welded at one end to the inertial flow tube 19 and has a female pipe thread at the other to match the inlet thread 39 of the eductor pump. The assembly provides a smooth, unbroken flow path from the inertial filter flow tube 19 through the eductor pump 40 to the system exit 41. The eductor pump 40 is of a clear path design, with motive air or fluid coming into the educator 40 radially through a fitting 42 extending therefrom. The sample or duct gas plus motive fluid then exits through the system exit 41 into the stack or duct.

An additional, optional construction to prevent particulate buildup on filter element 13 is a delivery tube 22 which may be provided within the sampling system to allow blowback air to be introduced from an external supply (not shown). By providing a tangential conduit 48 through support flange 45 connected to the interior of the probe 100, a flow path is formed between the sample gas extension tube 15 and an interior tube 29. The flow path is sealed at the flange end by the inertial filter flange 16 which is held in position when the probe body is retained by the attachment studs 46 attached to the flange 45, forcing the flange against retained O-ring 49. By attaching appropriate valving to the female pipe fitting 47, high pressure air or fluid can be forced to flow down delivery tube 22, through the sampling slit 23, through the inertial filter annulus 20 and eductor pump 40 and out the system exit 41. In addition to the use of blowback air, or alternatively to increase flow velocity past the filter element 13, the pressure of the regulated motive force fluid to the eductor 40 can be increased to a maximum of 80 psig, creating a flow volume of about 6 cu. ft./min, thus increasing the velocity past the inertial filter element by a factor of three times. In combination, the pressurized blowback fluid and increase in eductor flow can bring the velocity to three times the original velocity, or to 240 feet per second.

The delivery tube 22 can also be used for system bias checks by replacing the blowback fluid with a calibration gas or liquid. When operated in this manner, the motive gas to the eductor 40 is shut off and calibration gas is introduced through the pipe fitting 47 at a rate approximately 2 to 4 times the extraction sample rate coming out of the flange port 44. This action forces calibration gas down the delivery tube 22, out the sampling slit 23, down the inertial filter annulus 20 between the media in the inertial filter element 13 and the inertial filter flow tube 19, through the eductor 40 and out the system exit 41, completely displacing all stack or duct gas or liquid with a known concentration of calibration gas. System sampling continues with sample gas being drawn through the filter element 13, and through whatever filter cake may be present on the filter element 13, down extension tube 15 and out the flange port 44 of the probe body, to an externally mounted sample gas conditioning system and/or analyzers. By comparing the analysis of this through-system calibration gas reading with the reading obtained when the calibration gas flows directly to the analyzer an indication of the overall system bias can be obtained.

Maintenance is reduced by providing an arrangement which is a reversal of the method of construction of conventional inertial filters. Typically in prior inertial filter systems, the stack or duct gases flow down the center of a sintered metal filter element that is encased in a surrounding structure with gas to be sampled being drawn tangentially through the filter into the annulus or space formed between the filter element and the surrounding structure and then on to conditioning and/or analysis.

FIGS. 7 and 8 show the filter element 13, the extension tube 15 and two different methods of attachment of the probe head. FIG. 7 shows an inertial filter assembly 102 having a probe head that connects with an ISO fitting 17 welded to the end of the extension tube 15. An o-ring 18 is provided to form a seal against the mounting flange 45. FIG. 8 shows a flange seal probe with a probe head that uses a gasket seal between the head and the mounting flange 45. A plate forming the filter flange 16 is welded to the end of the extension tube 15. For this arrangement, a locking point or positioning pin 59 is included in the flange plate to prevent the entire assembly from rotating in the probe 100.

To replace the first inertial filter assembly 102 of FIG. 7, external probe head components (not shown) such as a hand knob at the end of a polishing filter is loosened and the cap removed. The filter is simply pulled from inside the probe body. For the flange seal probe 104 of FIG. 8, a probe head is unbolted from the attachment studs 46 and the filter flange 16 is simply pulled from the support flange 45. To replace either probe the procedure is reversed.

If the length of the spool 9 extending from the stack wall 10 is substantial, the sample gas traveling down the extension tube 15 may cool below acid dew point, water dew point or ammonia salt crystallization temperature before it can be conditioned. If this is a possibility, the annulus 31 between the body tube 28 and the internal tube 29 can be temperature controlled using a cable heater 32 coiled therethrough and a temperature measuring device 33 placed within the body tube 28 and wired to an external conduit box 34.

FIG. 6 shows the face of the support flange 45 and the various flow channels through the flange. Blowback and bias calibration are conducted through the pipe entrance fitting 47, motive fluid is transported to the eductor pump 40 through the flange connection 61, and the vacuum at the entrance to the eductor pump 40 is measured at exit fitting 60. Electrical connections for the monitoring and control of barrel temperature occur in conduit box 34. The extension tube 15 and the filter flange 16 are shown in the assembled positioned with the locking point or retainer pin 59 fixing the desired relationship between the inertial filter sealed edges 58 and the inlet standoffs 27.

Optimal operation of an inertial system is attained when particulate buildup is prevented anywhere alone the stack or duct gas flow path. The details of the pneumatically "smooth" path in the preferred embodiment intended to attain this objective are best shown in FIG. 2. Stack or duct gas enters the system through sampling slit 23 which exists radially around the probe. Three bolts 25 hold the upstream flow collet 26 and the downstream flow collet 24 together with the three standoffs 27 held therebetween. The three open areas between the standoffs 27 feed into the delivery tube 22 along smooth flow path 21. Each area connects with an inertial filter annulus 20 formed between the sealed edges 58 of the filter elements and the inertial filter flow tube 19. The radial location of the sealed edges 58 of the filter are positioned to correspond to the location of the bolts 25 and the standoffs 27 when assembled and this relationship is held in place by locking point 59 or, alternatively, a retainer pin in the same location. By knowing the area of the three inertial filter annuli 20 segments and the required linear flow rate, the Reynolds's Number of the flowing gases can be calculated. By choosing an appropriate cross sectional area profile, such as shown in the filter assemblies 54, 55 and 56 of FIGS. 3, 4 and 5, and a desired eductor pump 40 flow rate, the linear flow can be maintained fully turbulent inside the annuli 20 to assist in keeping filter element 13 clean. Once the sampled gas is past the filter element, a reconverging cone shape of the tail piece 14 brings the three streams together into the transition piece 35 located between the inertial flow tube 19 and the eductor pump 40 without undue disturbance. The coupler wall 36 creates a smooth transition between the flow tube 19 and the entrance to the eductor pump 40. Also, located in the same area is a pressure sampling port 37 on the end of a transmission tube 38 extending through the support flange 45 at fitting 60. A preferred eductor pump 40 is a "through" design, with no impairments to particulate flow visible through the bore, identified as an Air Vac TD260LSS. The described assemblies allow the particles to make one long clean sweep of the system, starting at sampling slit 23 and ending at the system exit 41 at the end of the eductor pump 40. The pressure at the entrance to the eductor 40 can be monitored at exit fitting 60. An increase in the vacuum level indicates that particulate accumulation is occurring somewhere along the flow path and signals the need for an inertial filter and/or system blowback.

It can thus be seen that a novel system and method of extractive gas sampling for the analysis of process gases or stack gases have been provided. The in-stack, pneumatically smooth, reverse inertial filter design minimizes changes in stack or duct kinetics, minimizes particulate buildup on any surface in the system, minimizes sample gas contact with any accumulated filter cake and provides for effort free parts replacement if needed. A blowback system, combined with an eductor pressure override, increases linear flows for efficient cleaning of inertial filter surfaces. A unique inertial filter cross-section design allows for economy of motive gas delivered to the eductor while providing maximum particulate removal with minimum buildup on the surface. Heating of the collected sample gas as it exits unheated sample port spools keeps the system moisture, acid and crystal free. Monitoring the vacuum at the eductor allows for automated blowback if any accumulation occurs. The ability to add calibration gas to the outside of the inertial filter assures that accurate sample bias values can be developed for the system—assuring continuing accuracy and analyzer uptime.

We claim:

1. A system for removing particulates and obtaining gas samples from a flowing gaseous stream located in a confined space, said gas stream exiting from a reaction or processing chambers comprising an inertial filter assembly mounted on a hollow probe positioned substantially perpendicular to and within said confined flowing gaseous stream, a portion of the gaseous stream being caused to flow along an annulus and through a longitudinally oriented filter media within the inertial filter assembly into an internal tubular space within the filter assembly, the filter media selected to allow gases to be sampled to pass there through while preventing particulate matter from passing there through, the portion of the gaseous stream so filtered passing along the internal tubular space and into and along the length of a central space in the hollow probe to a collection, sampling or analysis system external of the confined space.

2. The system of claim 1 wherein the inertial filter assembly comprises a hollow tube with a filter media mounted therein, the filter media extending the length of the hollow tube and enclosing the internal tubular space in the tube,
   a) the annulus comprising an annular space between the filter media and an inner wall of the tube, and
   b) the internal tubular space centrally located within the hollow tube to receive a gaseous sample passing through the filter media.

3. The system of claim 2 wherein the filter media contacts the inner wall of the tube in at least three locations substantially equally spaced along the circumference of the inner wall.

4. The system of claim 3 wherein the filter media is in the form of an elongated three-sided hollow structure having three substantially equal length side walls which extend between three apexes, the apexes contacting the tube inner wall, the dimensions of the side walls chosen to provide a desired filter area and to define the annular space with a desired volume for receiving flow of the gaseous stream portion.

5. The system of claim 1 wherein the filter media has pores with diameters from about 0.2 to about 2.0 microns.

6. The system of claim 4 wherein the annular space has a cross-sectional area from about 0.05 to about 0.1 in$^2$.

7. The system of claim 5 wherein the filter media is formed into a three sided hollow structure and the dimensions thereof are chosen to provide a volume flow through the annular space of from about 1.8 to about 3.4 ft$^3$/min at a flow velocity of about 80 ft/sec.

8. The system of claim 5 wherein the filter media is formed into a three sided hollow structure and the dimensions thereof are chosen so that gas passing through the annular space exhibits turbulent flow.

9. The system of claim 1 additionally including heat delivery means and temperature control means to maintain the temperature of the portion of the sampled gas in the probe at substantially the same temperature as the flowing gaseous stream passing through the confined space.

10. The system of claim 1 additionally including means for providing air from an external supply to the annular space to remove retained particulate matter.

11. The system of claim 1 additionally including means for providing a gas stream of known concentration to the annular space for calibration of the sampling system.

12. A method of obtaining stack gas for analysis and measurement of the constituents thereof comprising:
   placing a probe containing an inertial filter assembly within a flowing stream of stack gas,
   causing the stack gas to flow along an annular space within the inertial filter assembly and through a longitudinally oriented filter media to provide a filtered stack gas in a space interior to the filter media and within the filter assembly,
   moving such filtered gas from the interior of the inertial filter assembly along the length of the probe while maintaining said filtered stack gas at substantially the same temperature as the unfiltered stack gas, and
   delivering the filtered stack gas to a sampling device located external of the confined flow path containing the flowing gaseous stream.

13. The method of claim 12 additionally including providing air from an external supply to the annular space to remove retained particular matter.

14. The method of claim 12 additionally including providing a gas stream of known concentration to the annular space for calibration of the sampling system.

15. A system for obtaining substantially particulate free, gaseous samples from a flowing flue gas stream comprising a hollow probe with an inertial filter assembly attached thereto, the probe and filter assembly combination forming a gas sample collection device, the gas sample collection device configured to be mounted in the flowing flue gas stream with a sample outlet external of the flue gas stream, the filter assembly oriented so that a portion of the gaseous stream flows serially through a sampling port into the sampling device, along an annulus formed in the inertial filter assembly, through a longitudinally oriented filter media within the filter assembly into an internal tubular space within the filter assembly and through the hollow probe and sample outlet to an external collection, sampling or analysis system, the filter media selected to allow desired gases to pass into the internal tubular space while preventing particulate matter from passing there through, the particulate matter exiting the annular space and returning to the flowing flue gas stream.

16. The system for obtaining gaseous samples of claim 15 wherein the inertial filter assembly comprises a hollow tube with a three-sided filter formed of the longitudinally oriented filter media mounted therein and extending the length thereof, the filter media comprising the three-sided filter enclosing the internal tubular space in the tube, the annulus comprising an annular space between the filter media and an inner wall of the tube.

* * * * *